(12) United States Patent
Kotian et al.

(10) Patent No.: US 9,449,580 B2
(45) Date of Patent: Sep. 20, 2016

(54) IMAGE DISPLAY METHOD

(71) Applicant: General Electric Company, Schenectady, NY (US)

(72) Inventors: François Kotian, Vilepreux (FR); Régis Vaillant, Buc (FR); Maxime Cazalas, Buc (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 498 days.

(21) Appl. No.: 13/923,689

(22) Filed: Jun. 21, 2013

(65) Prior Publication Data
US 2013/0342524 A1 Dec. 26, 2013

(30) Foreign Application Priority Data

Jun. 25, 2012 (EP) ..................................... 12305734

(51) Int. Cl.
A61B 6/00 (2006.01)
G09G 5/14 (2006.01)
A61B 6/06 (2006.01)
G21K 1/04 (2006.01)

(52) U.S. Cl.
CPC . *G09G 5/14* (2013.01); *A61B 6/06* (2013.01); *A61B 6/463* (2013.01); *A61B 6/464* (2013.01); *A61B 6/486* (2013.01); *G21K 1/04* (2013.01)

(58) Field of Classification Search
CPC ........ A61B 6/06; A61B 6/405; A61B 6/486; A61B 6/487; A61B 6/488; A61B 6/54; A61B 6/542; A61B 6/547; G21K 1/04; G21K 1/043; G21K 1/046
See application file for complete search history.

(56) References Cited

U.S. PATENT DOCUMENTS

| 4,672,651 A * | 6/1987 | Horiba .................. A61B 6/481 348/E5.089 |
| 5,394,455 A | 2/1995 | Roeck et al. |
| 5,412,704 A | 5/1995 | Horbaschek |
| 5,459,769 A * | 10/1995 | Brown ................... A61B 6/032 378/16 |
| 7,085,343 B2 * | 8/2006 | Shinno .................. A61B 6/032 378/19 |
| 7,340,033 B2 | 3/2008 | Mollus et al. |
| 7,526,065 B2 * | 4/2009 | Hardesty ............... A61B 6/542 378/145 |
| 7,539,284 B2 | 5/2009 | Besson |
| 7,697,658 B2 * | 4/2010 | Wang ................... G06T 11/006 378/4 |

(Continued)

FOREIGN PATENT DOCUMENTS

| DE | 102010038916 A1 | 2/2012 | |
| EP | 2680677 A1 * | 1/2014 | ............... G09G 5/14 |

OTHER PUBLICATIONS

Search Report and Written Opinion from corresponding EP application No. 12305734.1, dated Nov. 28, 2012.

*Primary Examiner* — Thomas R Artman
(74) *Attorney, Agent, or Firm* — GE Global Patent Operation; Marc A. Vivenzio

(57) ABSTRACT

An image display method comprising displaying a first image of an imaged zone in a first display window and displaying a second image of only a part of the imaged zone in a second display window (S2) distinct from the first display window, and refreshing a majority of the first image at a first refreshing rate that is lower than a second refreshing rate of the second image.

17 Claims, 2 Drawing Sheets

(56) References Cited

U.S. PATENT DOCUMENTS

| | | | | |
|---|---|---|---|---|
| 7,983,391 B2* | 7/2011 | Machan | ............... | A61B 6/06 378/151 |
| 8,218,727 B2* | 7/2012 | Baumgart | ............... | G06T 19/00 378/98 |
| 9,131,908 B2* | 9/2015 | Shimizu | ............... | A61B 6/022 |
| 2004/0114706 A1* | 6/2004 | Ikeda | ............... | A61B 6/032 378/4 |
| 2005/0169428 A1* | 8/2005 | Hardesty | ............... | G01N 23/04 378/110 |
| 2005/0238140 A1* | 10/2005 | Hardesty | ............... | G01N 23/04 378/110 |
| 2006/0203966 A1* | 9/2006 | Mollus | ............... | A61B 6/06 378/150 |
| 2011/0058653 A1* | 3/2011 | Baumgart | ............... | G06T 19/00 378/98.2 |
| 2013/0342524 A1* | 12/2013 | Kotian | ............... | G09G 5/14 345/214 |

* cited by examiner

IMAGE DISPLAY METHOD

FIELD OF THE INVENTION

Embodiments of the present invention relate to image display methods and, more particularly, to image display methods focusing on a region of interest (ROI) of an imaged zone within a more extended field of view (FOV) of this imaged zone. In an embodiment of the present invention, the imaged zone can be part of a body of a human being. The imaged zone can be a part of an object exposed to a radiation source. Radiation can be X-ray radiation, but sources using other types of radiation can be used.

BACKGROUND OF THE INVENTION

While imaging part of a body of a human being, the amount of radiation emitted by the source and received by patients whose body is imaged as well as operators manipulating the imaging system, should be reduced. Therefore, to reduce the amount of radiation received by the patient, one efficient way is to limit the exposure of the anatomical part of body to be imaged.

Minimizing the amount of ionizing radiation used during x-ray guided interventional procedure is of importance to protect both patients and operators. Several strategies can be used as part of standard radiation protection practice. In particular, collimating the x-ray beam to limit exposure to the anatomical region being treated is very effective as it limits the x-ray beam to the required area. However, this comes at the expense of not being able to see the surrounding anatomical context. In addition, collimating to the right anatomical area requires operator action. This is the reason why collimation is often underutilized, thus leading to larger than necessary exposed area.

Currently, it is known to display one image showing at the same time the whole field of view of imaged zone as well as the more limited region of interest in the middle of the field of view. To be able to limit radiation exposure and frequently update information on the region of interest, the refreshing rate of the region of interest of the imaged zone is notably higher than the refreshing rate of the rest of the field of view surrounding the region of interest of the imaged zone.

However, even if satisfactory at first sight, this method has several drawbacks. When displaying the region of interest and field of view of an imaged zone in a single image on a single display window, the region of interest being within the center of field of view, choosing the size of the image to be displayed leads to a compromise. Either a limited size of displayed image is chosen or a big size of displayed image is chosen. If a limited size of displayed image is chosen, then the size of the displayed region of interest on the screen may be too small to be easily exploited by the operator. If a big size of displayed image is chosen, then the screen may be too cumbersome. Of course, a compromise can be chosen in between; but for the relatively big size of image, the size of the displayed region of interest on the screen may then appear as too narrow. Besides, in this method, the region of interest is not displayed in optimal conditions; indeed, the size of the displayed region of interest on the screen is too small.

SUMMARY OF THE INVENTION

An object of the present invention is to alleviate at least the above mentioned drawbacks.

More particularly, according to an embodiment of the present invention, an image display shows, on at least two different display windows of reasonable size, both the region of interest and the field of view, the region of interest being refreshed at a higher refreshing rate than the field of view. That way, both images can be optimized independently, the region of interest image so as to be easily exploited by the operator without needing too big a display window, and the field of view including the region of interest so as to locate the region of interest within the rest of field of view of imaged zone in a reasonable size display window, without impairing detailed exploitation of region of interest, since such detailed exploitation is no more performed in this display window.

An embodiment of the present invention comprises displaying a first image of an imaged zone in a first display window, displaying a second image of only part of said imaged zone in a second display window distinct from said first display window, a majority of said first image being refreshed at a lower refreshing rate than said second image. In an embodiment, all said first image is refreshed at a lower refreshing rate than said second image.

An embodiment of the present invention comprises a first display window adapted to display a first image of an imaged zone, a second display window, distinct from said first display window, adapted to display a second image of part of said imaged zone, a refreshing system adapted to refresh a majority of said first image at a lower refreshing rate than said second image. In an embodiment, all said first image is refreshed at a lower refreshing rate than said second image. More particularly, this image display system comprises a single collimating system which is adapted to collimate an electromagnetic beam which is sent on said imaged zone to capture said first and second images and which is also adapted to switch between said first and second images.

An embodiment of the present invention comprises an imaging system comprising a radiation source adapted to radiate on an imaged zone, a radiation detector adapted to receive radiation from said imaged zone so as to detect a first image of said imaged zone and a second image of only part of said imaged zone, and a collimating system adapted to collimate radiation emitted by said radiation source. The imaging system further comprises a control system adapted to control said collimating device so as to refresh a majority of said first image detected by said radiation detector at a lower refreshing rate than said second image detected by said radiation detector, and an image display system including a first display window adapted to display said first image received from said radiation detector and a second display window, distinct from said first display window, adapted to display said second image received from said radiation detector. In an embodiment, all said first image is refreshed at a lower refreshing rate than said second image.

Some embodiments comprise one or more of the following features, which may be taken separately or in partial combination or in full combination.

In an embodiment of the present invention, the first refreshing rate of the first image is at least twice smaller than the second refreshing rate of the second image or, in an embodiment, is at least five times smaller than the second refreshing rate of the second image or, in an embodiment, is at least ten times smaller than the second refreshing rate of the second image.

In an embodiment of the present invention, said first image is displayed on a first display screen and said second image is displayed on a second display screen distinct from said first display screen. That way, both screens can be kept in very reasonable range of size, one bigger screen may cost more than two smaller screens.

In an embodiment of the present invention, said second image is a zoom of only part of said first image. That way, while still keeping a reasonable size of display window and of associated screen, more optimal exploitation of information contained is said second image is made possible. In an embodiment of the present invention, said second image is displayed over a larger or equal screen area than said first image. That way, while still keeping a reasonable size of display window and of associated screen, even more optimal exploitation of information contained is said second image is made possible. Other image processing can be applied on one of the images and not on the other. Other image processing can be applied on both images but in a first way on first image which is different from a second way on second image.

In an embodiment of the present invention, a box framing said second image is displayed in said first image. That makes easier for the operator the quick location of region of interest within the rest of field of view.

In an embodiment of the present invention, said imaged zone is part of a body of a human being. In this field, the level of radiation received by the imaged zone if particularly critical. In an embodiment of the present invention, said imaged zone is imaged by medical X-ray imaging In an embodiment of the present invention, said imaged zone is imaged by medical dynamic X-ray imaging.

In an embodiment of the present invention, an electromagnetic beam collimated with a collimating system is sent on said imaged zone to capture said first and second images and switching between said first and second images is performed with same said collimating system. This saves material resources in the global imaging system. This is made possible by choosing a substantially lower refreshing rate for said first image showing field of view, since said field of view does not need such a high refreshing rate as region of interest, since it is to be used by the operator only from time to time and only to perform a rough localization of region of interest within field of view. In an embodiment of the present invention, said collimated electromagnetic beam is pulsed at a pulse rate corresponding to a pulse period, where a duration of opening or of shutting said collimating system is longer than the pulse period or, in an embodiment, is longer than two pulse periods or, in an embodiment, is longer than five pulse periods. The duration of opening and shutting said collimating system should not be too long. In an embodiment of the present invention, the duration of opening or of shutting said collimating system is shorter than twenty pulse periods or, in an embodiment, is shorter than ten pulse periods.

In an embodiment of the present invention, one or more pulses are not sent during opening and shutting of said collimating system. This allows avoiding emitting radiation that will produce intermediate images, images intermediate between region of interest and field of view, which indeed are not useful and need not be used by the operator. This helps make sure that all the radiation received by the imaged zone is "useful" radiation, which is radiation used to make images which are useful and which will be exploited by the operator, because those images are really needed and not only because those images have to be exploited since radiation has been emitted.

In an embodiment of the present invention, said first image is a single and full capture of said imaged zone, especially when one or more pulses are not sent during opening and shutting of said collimating system. Alternatively, said first image is a combination of several captured images, some of them containing only part of said imaged zone. This combination allows to refresh parts of field of view closer to region of interest to be refreshed more often than parts of field of view farther from region of interest, what can be useful, since the parts of field of view closer to region of interest are more critical than the parts of field of view farther from region of interest.

In an embodiment of the present invention, the first image is representing the field of view of an imaged zone and second image is representing a region of interest of the field of view of this imaged zone, the region of interest being smaller than the field of view and the region of interest being a portion only of the field of view, and the first image being refreshed at a first refreshing rate smaller than a second refreshing rate of second image. There are several embodiments for the refreshing rate of the region of interest located within the field of view in the first image.

In an embodiment of the present invention, the region of interest in the first image is refreshed at a first refreshing rate, that is, at the same refreshing rate that the rest of the field of view. Manipulation of information in the first image is rather simple and consistent between field of view and region of interest. However, region of interest is not updated as much as it could.

In an embodiment of the present invention, the region of interest in the first image is refreshed at a second refreshing rate, that is, at the same refreshing rate as the region of interest in the second image. The region of interest is updated as much as possible, but there may be some inconsistency between the region of interest and field of view, because of too big a difference between first and second refreshing rates.

In an embodiment of the present invention, the region of interest in the first image is refreshed at a third refreshing rate, this third refreshing rate being greater than the first refreshing rate but being smaller than the second refreshing rate. Region of interest updating is an intermediate between first and second embodiments, and there is a more consistency between region of interest and field of view than in second embodiment but less than in first embodiment. This intermediate value between first and second refreshing rates may help to make a better compromise in some cases.

In an embodiment of the present invention, capturing said first and second images is done by a detector, with no anti-scatter grid between imaged zone and detector. This option is specifically used when the part of a body which is x-rayed, is of reduced thickness.

In an embodiment of the present invention, the collimating system is switching between said first image showing field of view and said second image showing region of interest.

Said first image is being refreshed at a lower refreshing rate than said second image. To perform this in accordance with an embodiment of the present invention, at some periods, only part of the imaged zone is refreshed, whereas other parts of the imaged zone is not refreshed. In an embodiment of the present invention said other part of the imaged zone receives no or little imaging beam. This is done by one of interposing blades between imaging beam source and other part of image zone, and by interposing attenuating filters between imaging beam source and other part of image zone.

In an embodiment of the present invention, a means to automate collimation is proposed. Said means automates collimation to a reduced area and at the same time shows the region of interest in the broader anatomical context of the field of view of an imaged zone.

An embodiment of the present invention provides an imaging method comprising displaying a first image of an imaged zone and displaying a second image of only part of said imaged zone, said first image being refreshed at a lower refreshing rate than said second image. The method further comprises sending an electromagnetic beam collimated with a collimating system on said imaged zone to capture said first and second images and performing switching between said first and second images with same said collimating system. This imaging method can display both first and second images either on the same display window or on two display windows distinct from each other. If the already existing collimator in imaging system is reused to perform the switching between first and second image, this imaging method could be implemented in existing imaging system as a software only feature, thus resulting in no product cost increase, provided image processing resources can accommodate image pasting.

An embodiment of the invention provides an image display method. The image display method comprises displaying a first image of an imaged zone in a first display window; displaying a second image of only a part of the imaged zone in a second display window distinct from the first display window; and refreshing a majority of the first image at a first refreshing rate that is lower than a second refreshing rate of the second image.

An embodiment of the invention provides an image display system. The image display system comprises a first display window configured to display a first image of an imaged zone; a second display window, distinct from the first display window, configured to display a second image of only a part of the imaged zone; and a refreshing system configured to refresh a majority of the first image at a first refreshing rate that is lower than a second refreshing rate of the second image.

An embodiment of the invention provides an image system. The image system comprises a radiation source configured to radiate on an imaged zone, a radiation detector configured to receive radiation from the imaged zone so as to detect a first image of the imaged zone and a second image of only a part of the imaged zone, and a collimating system configured to collimate radiation emitted by the radiation source. The image system further comprises a control system configured to control the collimating device so as to refresh a majority of the first image detected by the radiation detector at a first refreshing rate that is lower than a second refreshing rate of the second image detected by the radiation detector, and an image display system. The image display system comprises a first display window configured to display the first image received from the radiation detector, and a second display window, distinct from the first display window, configured to display the second image received from the radiation detector.

Further features and advantages of the present invention will appear from the following description of embodiments of the present invention, given as non-limiting examples, with reference to the accompanying drawings listed hereunder.

DETAILED DESCRIPTION OF THE INVENTION

All FIGS. 1 to 6 are shown with a region of interest (ROI) which is a centered square of the field of view (FOV). Nevertheless, other suitable ways of delimiting the region of interest ROI in the field of view FOV, for example a non-centered rectangle, may be used.

Figure 1:
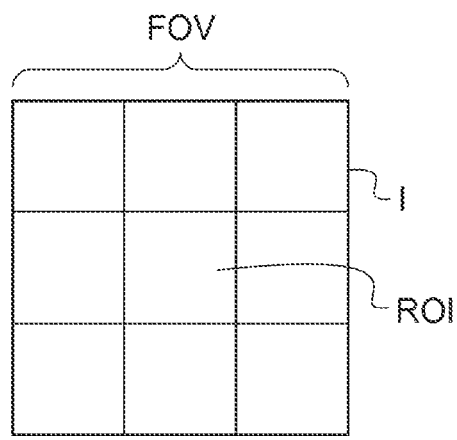
FIG. 1 shows an example of an image including a region of interest within a field of view according to some embodiments of the present invention.

FIG. 1 shows an example of image including a region of interest ROI within a field of view FOV according to some embodiments of the present invention. An imaged zone I corresponds to a field of view FOV including in its center a region of interest ROI. The field of view FOV covers 100% of the imaged zone I. The rest of the field of view FOV corresponds to the periphery of the imaged zone surrounding the region of interest ROI. Here the region of interest ROI covers about 11% of the whole field of view FOV, whereas the rest of the field of view FOV covers about 89% of the whole field of view FOV which corresponds to the imaged zone I.

Figure 2:
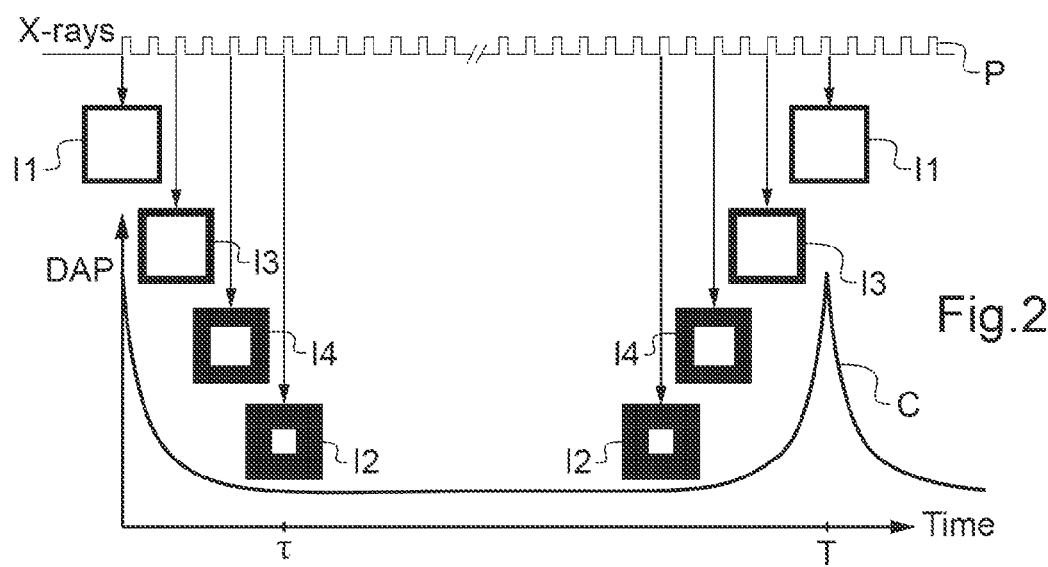
FIG. 2 shows an example of closing and opening of a collimating device to make first and second images to be displayed according to some embodiments of the present invention.

FIG. 2 shows an example of a closing and opening of a collimating device to make first and second images to be displayed according to some embodiments of the present invention. An Interventional x-ray imaging system will be operated in a new mode, in particular to make use of an off-the-shelf collimator and a new display mode. X-ray radiation is pulsed at pulse rate P. The collimator will close and open cyclically during exposure. The global cyclic period is T which, for example, ranges from 5 s to 10 s. The closing and opening duration is τ which, for example, ranges from 0.5 s to 1 s. During the closing period, the imaged zone goes from I1 corresponding to the complete field of view FOV to I2 corresponding to the region of interest ROI, going through the intermediate images I3 and I4. During opening period, the imaged zone goes from I2 corresponding to the region of interest ROI to I1 corresponding to the complete field of view FOV, going through the intermediate images I4 and I3.

Indeed, soon after the operator depresses the x-ray pedal to start imaging the patient, the collimator blades automatically move until reaching a defined region of interest ROI position corresponding to image I2. It is not the object of the present invention to specifically describe how the region of interest ROI is selected, especially its size and position. It can simply be a zone located at the center of the image whose area is, e.g., $1/4^{th}$ to on $1/9^{th}$ of the full field of view FOV. Another form, different from a centered square, can be used too, for example a non-centered rectangle, or a centered rectangle or a non-centered square. Although it is desirable that the collimation blades move quickly from the full field of view FOV position corresponding to the image I1 to the region of interest ROI corresponding to the image I2 position, it is not necessary that this happens between two x-ray exposures, e.g. sixty-seven (67) milliseconds if the patient is imaged at fifteen (15) images per second. While the collimation blades close, the image processor of the x-ray system keeps memory of successive images, here for example images I3 and I4, and, in a given image, replaces the dark area due to the presence of the collimator blades by the most recent image information available prior to the blades reaching this position.

This allows showing the region of interest ROI at a nominal frame rate in its broader anatomical context encompassing the full field of view FOV. As this information can become quickly irrelevant because of natural anatomical motion or because the operator wants to image a different zone, the collimator will open to the full field of view FOV every few seconds automatically, or based on changes of imaging conditions, such as table top or gantry motion, or under a specific operator action, such as a change of the field of view FOV size, a change of the region of interest ROI size or position, etc. During this process, the image is refreshed using the same process as already described. This process is repeated as the operator continues pressing the x-ray pedal. Typically, the collimator may close or open within half a second and the process may be repeated every 5 seconds. The curve (C) shows the Dose Area Product (DAP) plotted versus time.

Although this is not the object of the present invention to present specific image processing algorithms, two possible, simple implementations of the processing to eliminate the collimator blades from the image are mentioned. The first one is a form of peak detection that retains the maximum pixel value outside the region of interest ROI. Another possibility is a modified traditional fluoroscopic noise reduction filter which is a recursive low pass filter. Obviously, more sophisticated processing is possible.

Figure 3:
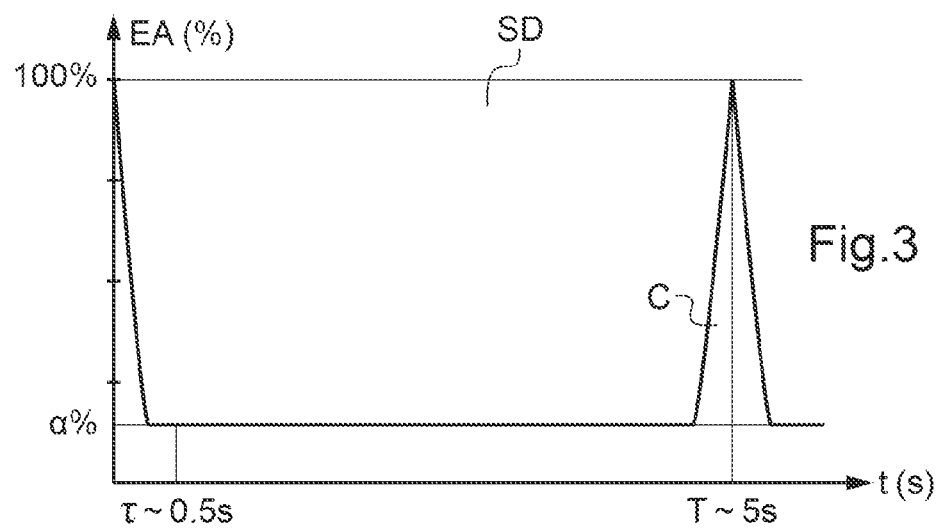
FIG. 3 shows a curve showing the radiation dose reduction when using different refreshing rates for first and second images to be displayed according to some embodiments of the present invention.

FIG. 3 shows a curve showing the radiation dose reduction when using different refreshing rates for first and second images to be displayed according to some embodiments of the present invention. The duration of opening or of shutting said collimating system is notably longer than the pulse period. The curve C of FIG. 2 is shown again, whereas the saved dose (SD) of radiation received by the imaged zone is shown too. The exposed area (EA), expressed in percentage, is plotted versus the time, expressed in seconds. Clearly, refreshing the full field of view FOV at a notable lower rate than the region of interest ROI allows for a notably high saved dose.

Interestingly enough, this mode can allow operating without an anti-scatter grid. When the exposed area becomes small, typically 12 cm or less, it becomes advantageous to remove the anti-scatter grid for small patient thickness, because scatter rejection will not so easily make up for the signal loss due to grid absorption. Indeed, contrast-to-noise can be made better without grid at equivalent image quality and lower dose, in about a 10-20% range. Therefore, the proposed scheme could at the same time provide lower Dose Area Product (DAP), representative of the level of radiation received by the imaged zone, and lower skin dose in some circumstances, particularly in pediatric imaging. The curve C is showing the level of this Dose Area Product (DAP) which of course is much greater during the closing and opening phase than during the region of interest ROI stable position.

Moreover, the proposed mode could be further leveraged to provide means for scatter radiation correction in the image. It is known in the art that scatter can be estimated by measuring a signal at the location of the collimator blades. Then correction can be applied to the region of interest ROI based on this measurement. One simple approach is to subtract the mean measurement from the readings at the region of interest ROI. Other more sophisticated methods exist.

Figures 4, 5:
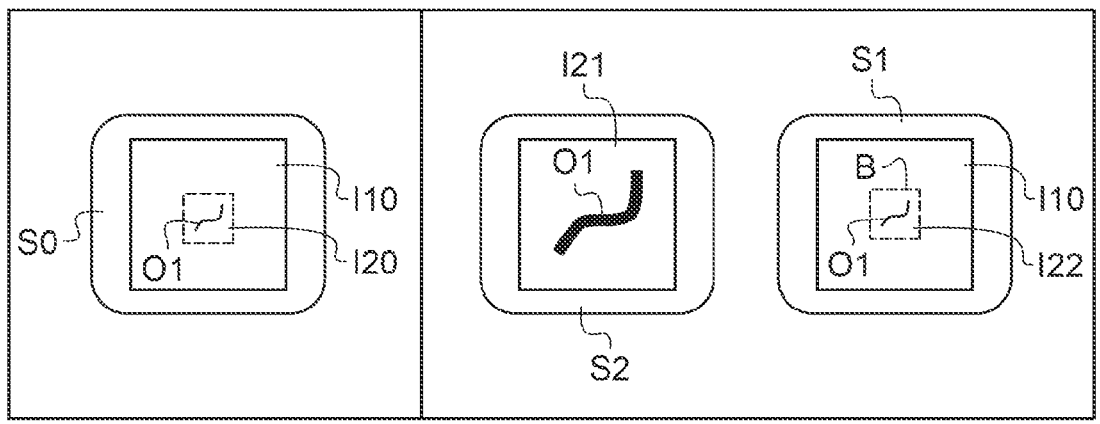
FIG. 4 shows an example of a displayed image according to the prior art.
FIG. 5 shows an example of displayed images according to some embodiments of the present invention.

FIG. 4 shows an example of a displayed image according to the prior art. On a screen (S0), in the same display window, a first image I10 representing the field of view FOV of an imaged zone is displayed. In the center of the first image I10, a second image I20 representing the region of interest ROI is displayed. In the second image I20, there is an object O1 that can be seen. This object O1 is relatively small, so if it is to be seen more clearly by the operator, the operator will have to zoom on the second image I20 which will cover at least part of the surrounding field of view FOV, which will then be no more visible by the operator. Part of first image I10 surrounding the second image I20 is refreshed at a lower rate than the second image I20. Such factors as low refreshing rate, pasting of images taken at different times, not clearly defined blade edges due to a non-punctual x-ray source as well as off-focal radiation, etc. will result in degradation of image quality, with exception of the region of interest ROI.

FIG. 5 shows an example of displayed images according to embodiments of the present invention. On a screen S1, or in a first display window of a given screen, a first image I10 representing the field of view FOV of an imaged zone is displayed. In the center of the first image I10, a second image I22 representing the region of interest ROI is displayed. In the second image I22, there is an object O1 that can be seen. This object O1 is relatively small, but it can be seen more precisely on a second screen S2, or in a second display window different from the first display window but on the same given screen. A second image I21 representing the region of interest ROI is also displayed; the second image may be zoomed in on Here, object O1 can be seen more clearly, especially with fewer artefacts or without any of the artefacts which can be created at the border B between the images I10 and I22.

Screen S1 is the reference monitor showing the region of interest ROI in the anatomical context of the field of view FOV. Screen S2 is the live monitor showing in detail and or without artefacts the region of interest ROI alone, independently of the field of view FOV. This is quite an interesting mode because the operator requires maximum image quality for the region of interest ROI and can get by with reduced quality for the anatomical background shown in the field of view FOV. The live image I21 is where the eye will focus and the reduced rate image I10 including image I22 will serve as a reference from time to time. The border B between the image I22 representing the region of interest ROI of first image I10 and the rest of the image I10 may be indicated by graphics on the first image I10, for example through a dotted box framing B. From a practical standpoint, two different monitors may be used, or alternatively, a large monitor screen with two fully distinct display windows, one for the first image I10 including image I22, and the other one for the second image I21.

Figure 6:
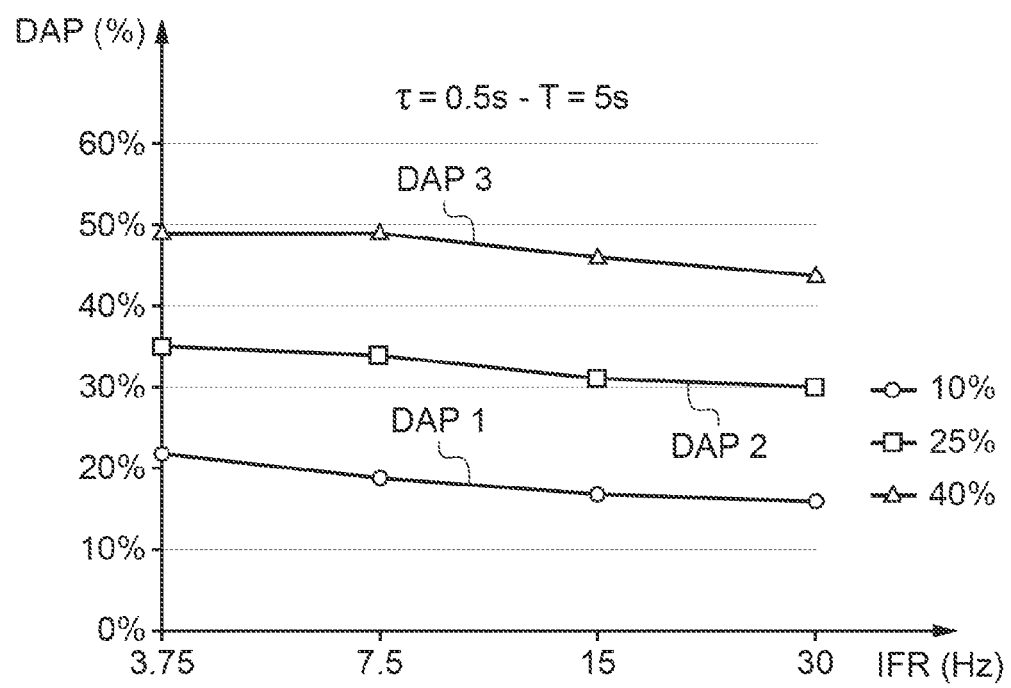
FIG. 6 shows examples of curves showing the evolution of the resulting Dose Area Product with respect to the frame rate between second image and first image according to some embodiments of the present invention.

FIG. 6 shows examples of curves showing the evolution of the resulting Dose Area Product (DAP) with respect to the frame rate between the second image and the first image. The duration of opening or shutting said collimating system is notably longer than the pulse period. The resulting DAP, expressed in percentage, is plotted versus the image frame rate IRF, expressed in Hertz. Resulting DAP shows the percentage of DAP remaining versus the nominal DAP without the collimating system closing and opening. The three curves DAP1, DAP2 and DAP3, correspond respectively to three different ratios of surfaces between second image and first image, here 10%, 25% and 40%. The higher the ratio between the ROI and FOV areas is, the higher the resulting DAP is relative to the nominal DAP, while keeping in mind that the resulting DAP remains inferior to the nominal DAP, without collimation opening and closing, and the lowest is also the factor by which the nominal DAP is divided.

The exposed area of the patient is limited. Radiation is not reduced at the region of interest ROI, with exception of the proposed removal of the anti-scatter grid, but unnecessary exposure to surrounding anatomy is limited. From a practical standpoint, this will provide significant reduction of the DAP. At first order (not accounting for the discrete nature of the x-ray exposure), DAP reduction as defined by the ratio of DAP in the automated region of interest ROI mode to DAP at the full field of view FOV can be approximated by the following equation:

$$DAP \text{ Reduction} \cong \alpha + \frac{2\tau}{T}\left(\frac{1}{3} - \alpha + \frac{2}{3}\alpha^{\frac{3}{2}}\right)$$

Where α is the ratio between the region of interest ROI and the full field of view FOV areas, T is the period of the close open collimator blade cycle, and τ is the time required by the collimator to fully close or open.

Using $\alpha=\frac{1}{9}$, T=5 s, τ=0.5 s: the resulting DAP is approximately 16% of nominal DAP. Therefore, such a mode can easily divide the DAP by a factor of 5, depending on characteristics of the collimator, for instance speed, area of the selected region of interest ROI, refreshing rate, and image frame rate. In particular, in very low frame rate modes, collimator closure can be viewed as occurring instantaneously between x-ray exposures, thus providing optimal dose reduction conditions.

This written description uses examples to disclose the present invention, including the best mode, and also to enable any person skilled in the art to practice the present invention, including making and using any computing system or systems and performing any incorporated methods. The patentable scope of the present invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of generating radiological images comprising:
    generating a first image by collimating radiation from a continuously pulsed radiation source onto an imaged zone using a first collimating configuration causing the first image to be refreshed at a first rate;
    generating a second image by collimating the radiation from the continuously pulsed radiation source onto only a part of the imaged zone using a second collimating configuration causing the second image at be refreshed a second rate,
    wherein the first rate is lower than the second rate, the radiation is pulsed at a pulse rate corresponding to a pulse period, and a duration of opening or of shutting a collimating system used to collimate the radiation is longer than at least one pulse period.

2. The method according to claim 1, wherein the first image is displayed on a first display screen, and the second image is displayed on a second display screen distinct from the first display screen.

3. The method according to claim 1, wherein the second image is a zoom of a part of the first image.

4. The method according to claim 1, wherein the second image is displayed over a larger or equal screen area than the first image.

5. The method according to claim 1, wherein a box framing the second image is displayed in the first image.

6. The method according to claim 1, wherein the imaged zone is a part of a body of a human being.

7. The method according to claim 1, wherein the imaged zone is imaged by a medical X-ray imaging.

8. The method according to claim 1, wherein the imaged zone is imaged by a medical dynamic X-ray imaging.

9. The method according to claim 1, wherein the duration of opening or of shutting the collimating system used to collimate the radiation is longer than two pulse periods.

10. The method according to claim 1, wherein one or more pulses are not sent during the opening and the shutting of the collimating system.

11. The method according to claim 1, wherein the first image is a combination of captured images, wherein some of the captured images contain only a part of the imaged zone.

12. The method according to claim 1, wherein the first image is a single and full capture of the imaged zone.

13. The method according to claim 1, wherein at least an image processing correction is applied on the second image only and not on the first image.

14. The method according to claim 1, comprising displaying the first image in a first display window and displaying he second image in a second display window distinct from the first display window.

15. An image generation system comprising:
    a collimator comprising:
        a first configuration for collimating radiation from a continuously pulsed radiation source onto an imaged zone to generate a first image; and
        a second configuration for collimating the radiation from the continuously pulsed radiation source onto only a part of the imaged zone to generate a second image,
        wherein the first collimating configuration is operable to cause the first image to be refreshed at a first rate and the second collimating configuration is operable to cause the second image be refreshed at a second rate that is higher than the first rate, the radiation is pulsed at a pulse rate corresponding to a pulse period, and a duration of opening or of shutting a collimating system used to collimate the radiation is longer than at least one pulse period.

16. The image generation system of claim 15, comprising a first display window for displaying the first image and a second display window distinct from the first display window for displaying the second image.

17. An image system comprising:
    a continuously pulsed radiation source;
    a collimating system comprising:
        a first configuration for collimating radiation from the continuously pulsed radiation source onto an imaged zone to generate a first image; and a second configuration for collimating the radiation from the continuously pulsed radiation source onto only a part of the imaged zone to generate a second image, wherein the first collimating configuration is operable to cause the first image to be refreshed at a first rate and the second collimating configuration is operable to cause the second image be refreshed at a second rate that is higher than the first rate, the radiation is pulsed at a pulse rate corresponding to a pulse period, and a duration of opening or of shutting a collimating system used to collimate the radiation is longer than at least one pulse period; and an image display system comprising:
   a first display window configured to display the first image; and
   a second display window, distinct from the first display window, configured to display the second image.

* * * * *